United States Patent [19]

Verdickt

[11] 4,060,727
[45] Nov. 29, 1977

[54] METHOD AND APPARATUS FOR THE RADIOGRAPHIC INSPECTION OF TUBES

[75] Inventor: Jacques Verdickt, Dunkerque, France

[73] Assignee: Vallourec (Usines a Tubes de Lorraine-Escaut et Vallourec Reunies), Paris, France

[21] Appl. No.: 673,481

[22] Filed: Apr. 5, 1976

[30] Foreign Application Priority Data

Apr. 10, 1975 France .................................. 75.11220

[51] Int. Cl.² .......................................... G01M 21/00
[52] U.S. Cl. .................................. 250/358 P; 250/491
[58] Field of Search ............................. 250/358 P, 491

[56] References Cited

U.S. PATENT DOCUMENTS

| 2,965,758 | 12/1960 | Malick | 250/358 P |
| 3,087,058 | 4/1963 | Arvanetakis et al. | 250/358 P |
| 3,628,029 | 12/1971 | Tompkins | 250/358 P |

Primary Examiner—Harold A. Dixon
Attorney, Agent, or Firm—Brisebois & Kruger

[57] ABSTRACT

Apparatus for the radiographic inspection of tubes comprises a chamber containing a radiation emitter, a carriage for positioning a selected section of the tube opposite the emitter, a movable member for positioning a film inside the tube opposite the emitter, and a remote control system for operating the emitter, carriage, and movable member from outside the chamber. Method of making a film of a selected area of said tube with said apparatus.

7 Claims, 4 Drawing Figures

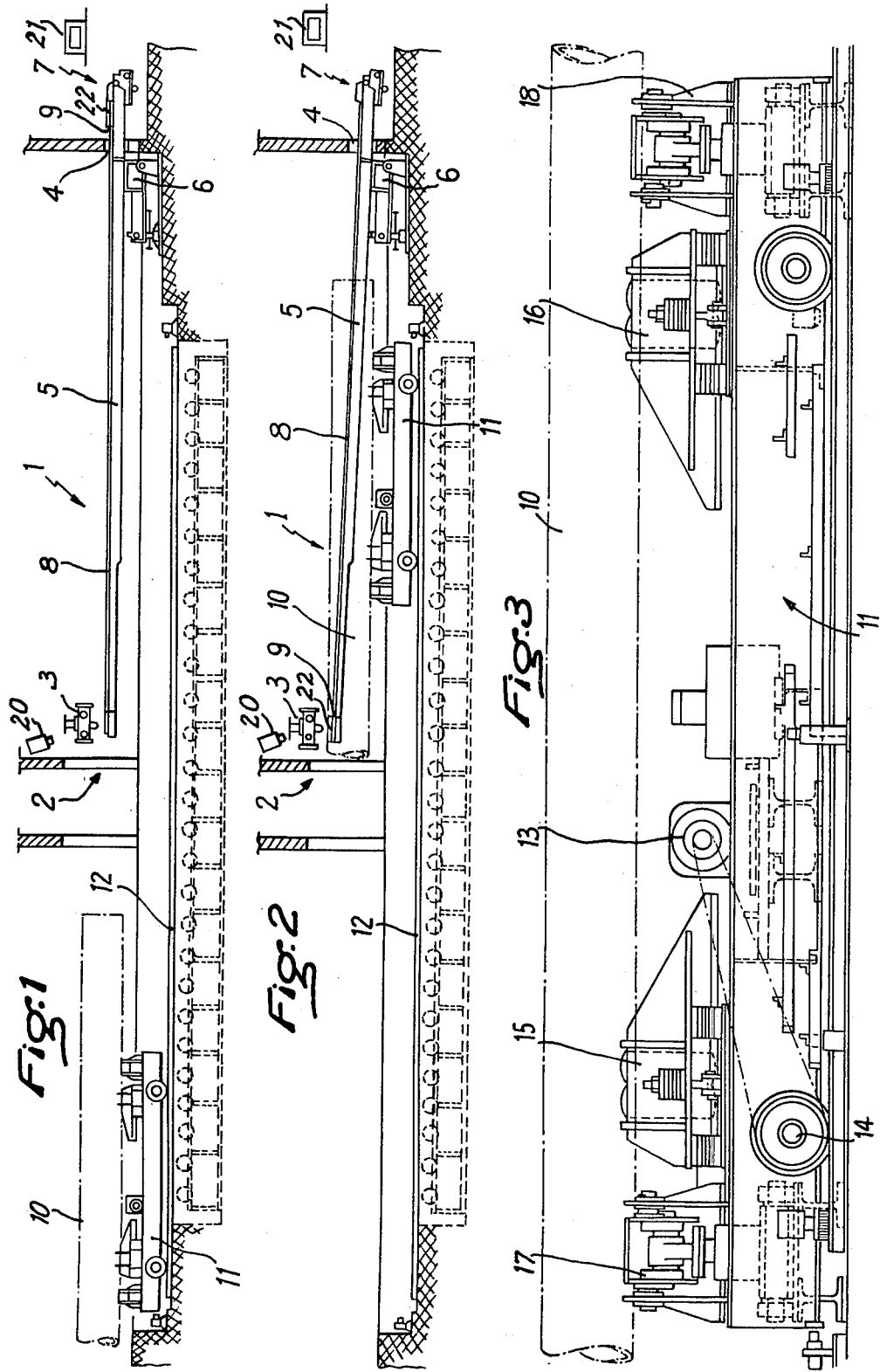

METHOD AND APPARATUS FOR THE RADIOGRAPHIC INSPECTION OF TUBES

SUMMARY OF THE INVENTION

This invention relates to a method and apparatus for radiographically inspecting tubes, which are particularly adapted to the control of the quality of welded tubes in an installation for producing welded tubes.

It is well known that the requirements which must be met during the use of tubes for the transportation of fluids or gas demand the manufacture of tubes having excellent mechanical strength and fluid tightness. It is thus necessary, in the case of welded tubes, to inspect the weld in the tube after its manufacture, and radiographic devices relying on X-rays or fluoroscopes are currently in use for this purpose.

In view of the danger which the radiation presents to the personnel required to handle the tubes, it is important that the radiographic operation be carried out so that the personnel need not enter the zone subjected to radiation. Moreover, because of the high speed of operation necessary in modern units for producing welded tubes, it is important that the radiographic step be carried out automatically so that it does not slow down the rate of production.

The present invention therefore relates to a method and apparatus for radiographically inspecting tubes, which meet these requirements.

The present invention relates particularly to a method of radiographically inspecting tubes characterized by the fact that the tube to be inspected is displaced in such a manner as to bring a presumably defective zone opposite a radiation emitter, a film sensitive to the radiation is introduced into said tube, and the film displaced to bring it opposite the radiation emitter, the radiation emitter is actuated to expose the film, after which the exposed film is removed from the tube.

Advantageously, after having brought the film opposite the radiation emitter, it is at this point pressed against the internal surface of the tube.

The presumably defective zone is localized and marked in the course of a preliminary inspection step, preferably by ultrasonic inspection, and the movements of the tube and the film are remotely controlled by an operator who, while watching the operation on a television circuit, moves the tube so as to bring the presumably defective zone marked, for example, by a symbol on the tube, opposite the radiation emitter. In a particular embodiment the radiation emitter is a source of X-rays.

According to the invention the presumably defective zone may advantageously be detected by continuously projecting a radioscopic image on a receiving screen, with the operator using the radiographic process to obtain a film of the presumably defective zone detected by radioscopy.

It is a further object of the present invention to provide a device for the radiographic inspection of tubes which may be used in carrying out the above process characterized by the fact that it comprises:

An elongated chamber provided with an opening at one end for the introduction of an inspection tube;

A rod penetrating said chamber through the end remote from said opening and extending substantially the full length of the chamber, said rod being provided with means for guiding a mobile film support along said rod;

A radiation emitter positioned inside said chamber;

A movable transport member for carrying tubes adapted to lead the tube to be inspected from the exterior of said chamber through said opening in said chamber so as to encircle the rod;

Means for controlling said transport member which may be actuated from outside the chamber to immobilize said transport member when the presumably defective zone of the tube is opposite the radiation emitter;

Control means for the film support adapted to be actuated from outside the chamber to displace this support between a first position in the vicinity of the end of the rod outside said chamber and a second position opposite the radiation emitter.

Advantageously the rod is pivotally mounted on a support positioned in said chamber opposite the opening for the introduction of the tubes. In this manner, by pivoting the rod, it is possible to press the film which is at the end of the rod against the zone to be radiographed.

In a particularly advantageous embodiment, means are provided to adjust the height of the radiation emitter with respect to the rod, the movements of the radiation emitter assuring that the axis of the beam of rays emitted is always substantially perpendicular to the plane of the film while the latter is being exposed.

The film support advantageously comprises a member in the form of a liner of foam material adapted to press the film smoothly against the internal surface of the tube during operation of the radiation emitter.

According to the invention, the device for transporting the tubes comprises at least one carriage movable on guide rails and equipped with guide means to support the tube and rotate it on itself, so as to permit any selected zone on its periphery to be positioned opposite the radiation emitter.

It will be appreciated that the process and apparatus according to the invention apply particularly well to the radiography of tubes having a longitudinal weld when it is desired to radiograph presumed defects at the level of the welded seam. It then suffices for an operator situated outside the radiographic chamber proper, who is watching the operation on a television screen, to rotate the tube about its own axis, utilizing guide means positioned on the tube-supporting carriage, so as to bring the welded seam opposite the radiation emitter, and then longitudinally displace the tube carrier so as to bring the marked zone of presumed defects directly opposite the radiation emitter.

By displacement of the film support the film to be exposed is then brought into the tube opposite the radiation emitter so that the tube zone to be radiographed is positioned between the radiation emitter and the film, after which the radiation emitter is actuated and the film support returned to the end of the rod outside the chamber so as to replace the exposed film with a blank film, after which the inspection operation is recommenced at another zone of the same tube or the next tube.

In order that the invention may be better understood, a preferred embodiment thereof will now be described, purely by way of illustration and example, with reference to the accompanying drawings in which:

FIG. 1 is a schematic side view of the device according to the invention before the introduction of the tube to be inspected;

FIG. 2 is a schematic side view of the device according to the invention in the course of operation;

FIG. 3 is a more detailed elevational view of a tube supporting carriage which may be used in carrying out the present invention.

Figure 4:
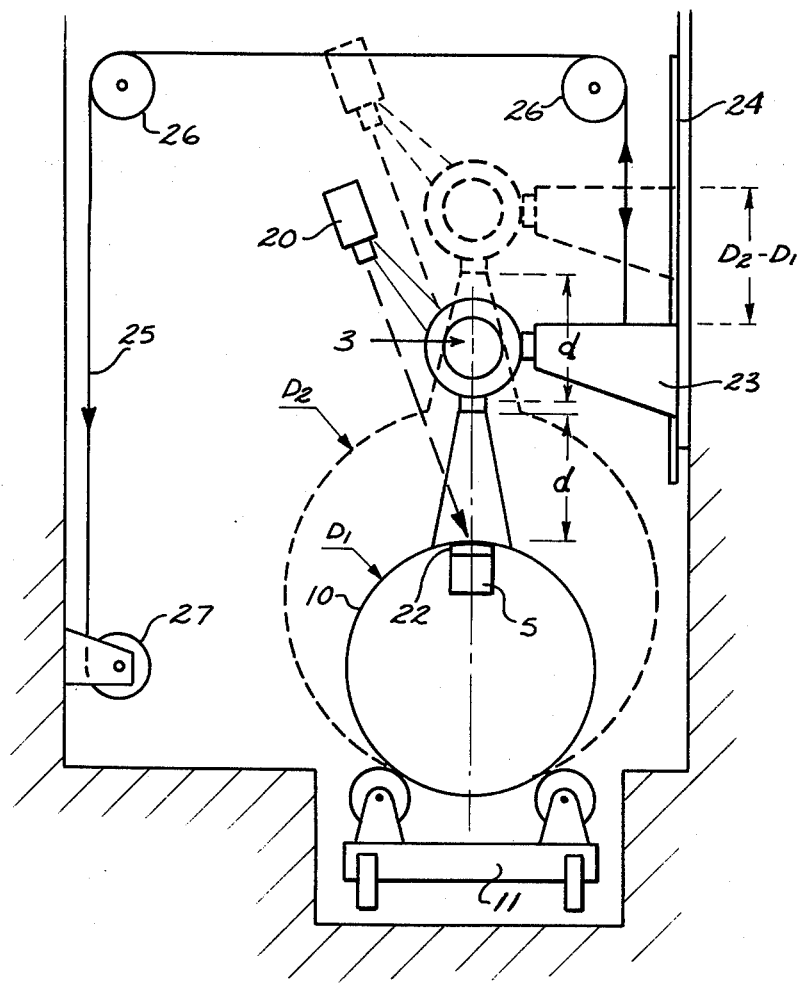
FIG. 4 is an end view of the device showing a height adjustment feature.

As may be seen on FIGS. 1 and 2, the device according to the invention comprises a tunnel chamber 1 provided at one of its ends with an opening 2.

Inside this chamber is a radiation source 3, for example a source of X-rays. This radiation source 3 is mounted so as to be movable up and down.

Through the end 4 of the chamber 1 opposite the opening 2 projects a rod 5 pivotally mounted on a support 6 near the end 4 of the chamber so that the inclination of the rod 5 with respect to the horizontal may be modified, for example, by means of an eccentric.

As shown on FIGS. 1 and 2, the rod 5 passes through the end 4 of the chamber 1 and extends into a chamber 7 which is isolated from the chamber 1 subjected to radiation emitted by the source 3. In the chamber 7 is an operator equipped with a television screen watching the interior of the chamber 1, in which television cameras (not shown) are located. In this chamber there is also a radioscopic receiver screen permitting the operator to continuously inspect the tube by radioscopy and make a radiography of presumably defective zones detected by radioscopy. Along its top the rod 5 carries a guide 8 along which a carriage 9 may be displaced. This carriage carries a plate of film sensitive to the radiation emitted by the source 3. This carriage is movable between a first position shown in FIG. 1 in chamber 7, outside the chamber 1, and a second position illustrated on FIG. 2, near the end of the rod 5 substantially opposite the radiation source 3. The tube 10 to be inspected is mounted on a tube supporting carriage, indicated generally by reference numeral 11, which is movable on guide rail 12.

The tube supporting carriage 11, which is best seen in FIG. 3, comprises a drive motor 13 connected to a drive shaft 14. At its upper part the carriage 11 carries guide members 15, 16 for the supported tubes. These members, which are known in themselves, support the tube 10 and are adapted to rotate it about its longitudinal axis so as to bring any selected peripheral zone thereof uppermost, especially the longitudinal welded seam when it is desired to inspect such a seam in the device according to the invention.

The carriage 11 is equipped with means 17 and 18, also known in themselves, for ejecting tubes, which are adapted to eject the tube 10 from the carriage 11 once the radiographic operation according to the invention has been completed.

The operation of the device illustrated on the drawing in carrying out the process according to the invention will now be described.

A tube 10, the defects in which have presumably already been located, for example in the course of an ultrazonic inspection step, is positioned on the tube supporting carriage 11. The operator in the chamber 7 then places a blank film on the movable carriage 9 at the end of the rod 5 in the chamber 7.

The operator then actuates the carriage 11 by remote control so that it travels along the guide rails 12 through the opening 2 in the chamber 1, so as to encircle the rod 5 as may be seen on FIG. 2. The operator, as a consequence of the surveillance carried out by a television camera 20 and a monitor 21 located in chamber 7, then rotates the tube about its own axis by means of guides 15 and 16, so as to bring the marked presumably defective zone opposite the radiation source 3, and the displacement of carriage 11 along its guide rails 12 is stopped when the marked zone is exactly opposite the radiation source 3. It will be appreciated that the emitter 3 and television camera are fixed to the same movable support, with the camera permanently focussed on a segment of a plane located at a predetermined distance in front of the emitter. As a variation, as already indicated, it is possible to carry out continuous radioscopic inspection of the tube 10 during displacement of the carriage 11 on the guide rails 12. The operator detects on the receiving screen the presumably defective zone and then immobilizes the tube 10 with the zone thus detected opposite the radiation source 3. At this moment the carriage 9 supporting the film is moved along its guide path 8 on the rod 5 so as to come into the position illustrated in FIG. 2 opposite the radiation source 3. The rod 5 is then swung around its pivot point 6 so as to press the film on the movable carriage 9 against the inner surface of the tube opposite the radiation source 3. To this end the film support may be provided with a lining of foam material 22 so as to be able to apply the film perfectly against the inner surface of the tube. The radiation source 3 is then actuated so as to capture on the film an image of the presumed defect. The film supporting carriage 9 is then returned along its path of travel 8 on the rod 5 to the end of the rod inside the chamber 7 where the operator retrieves the film for subsequent development and replaces it with a blank film. If the tube has other presumably defective zones the carriage 11 is displaced to bring these zones opposite the radiation source 3 and the operation is repeated. If the tube has no other presumably defective zones the carriage 11 is displaced so as to entirely remove the tube from the chamber 1 to the position shown on FIG. 1, in which the ejectors 17 and 18 of the carriage 11 are actuated so as to eject the tube. A new tube may then be located for inspection on the carriage 11 and the operation repeated.

The invention thus makes it possible to carry out the entire operation of radiographic inspection without the presence of personnel inside the chamber 1 which is subjected to radiation. The process according to the invention is especially applicable to the inspection of longitudinal welds in tubes but is not limited to this particular application since it may be used for the inspection of other types of welds, especially helical welds, or for the inspection of zones on the periphery of the tube outside the welded seam. It will accordingly be appreciated that the invention is not limited to a tube of any particular diameter, but may be applied to the inspection of tubes of any diameter. As shown in FIG. 4, radiation source 3 and television camera 20 are mounted on pedestal 23 which is moved up or down on guide rod 24 by cable 25 passing over pulleys 26 and around winch 27. For a pipe of diameter $D_1$, the unit is located in the position shown by solid lines. The dotted lines indicate the position of the unit for a larger pipe with diameter $D_2$. Moreover, because the vertical position of the radiation source may be adjusted with respect to the rod supporting the film it is possible to insure that, regardless of the inclination of the rod 5 required to apply the film against the internal surface of the tube 10, the axis of the beam of rays emitted by the source 3 remains perpendicular to the plane of the film so as to insure the production of a high quality print. Moreover, the invention is not limited to inspection by means of X-rays, but may be used with any type of radiation by selecting a suitable radiation source and film.

While only one particular embodiment of the invention has been described, it will be obvious that the scope of the invention is not limited to the details of that embodiment but may be modified as to detail without thereby departing from the basic principles of the invention.

What is claimed is:

1. Device for the radiographic inspection of tubes which comprises:

an elongated chamber provided with an opening for the introduction of a tube to be inspected;

a rod projecting from a point outside said chamber into said chamber opposite said opening and extending substantially the full length of the chamber, said rod being provided with means for guiding a mobile film support along the rod;

a radiation emitter positioned inside the chamber;

tube-transporting means for bringing a tube to be inspected from outside the chamber through said opening so as to encircle the rod, said tube transporting means comprising at least one carriage movable on guide rails and carrying means for rotating the tube about its own axis;

control means for said tube-transporting means adapted to be actuated from outside the chamber to immobilize said tube transporting means when a selected zone of the tube is opposite the radiation emitter;

and control means for said film support adapted to be actuated from outside the chamber to move said support from a first position near the end of said rod outside the chamber and a second position opposite said emitter.

2. Device as claimed in claim 1 in which the movements of the tube and film are remote controlled by means of a television circuit.

3. Device as claimed in claim 1 in which the radiation emitter is a source of X-rays.

4. Device as claimed in claim 1 in which said zone is a presumably defective zone detected by continuous radioscopy of the tube projected on a receiving screen.

5. Device as claimed in claim 1 in which said rod is mounted to pivot about a support positioned in said chamber at a point remote from the opening for introducing the tubes.

6. Device as claimed in claim 1 comprising means for adjusting the height of said radiation emitter with respect to said rod.

7. Device as claimed in claim 6 in which the film support comprises a supporting member in the form of a lining of foam material adapted to press the film against the internal surface of the tube.

* * * * *